United States Patent
Tiwari et al.

(10) Patent No.: US 10,849,530 B2
(45) Date of Patent: Dec. 1, 2020

(54) ELECTRONIC DEVICE AND METHOD FOR PROVIDING INFORMATION RELATED TO SKIN TYPE OF OBJECT

(71) Applicant: Samsung Electronics Co., Ltd., Gyeonggi-do (KR)

(72) Inventors: Vijay Narayan Tiwari, Bangalore (IN); Shankar M. Venkatesan, Bangalore (IN); Rangavittal Narayanan, Bangalore (IN)

(73) Assignee: Samsung Electronics Co., Ltd

( * ) Notice: Subject to any disclaimer, the term of this patent is extended or adjusted under 35 U.S.C. 154(b) by 56 days.

(21) Appl. No.: 15/742,808

(22) PCT Filed: Jul. 5, 2016

(86) PCT No.: PCT/KR2016/007260
§ 371 (c)(1),
(2) Date: Jan. 8, 2018

(87) PCT Pub. No.: WO2017/007218
PCT Pub. Date: Jan. 12, 2017

(65) Prior Publication Data
US 2018/0199856 A1    Jul. 19, 2018

(30) Foreign Application Priority Data

Jul. 8, 2015 (IN) ........................... 3495/CHE/2015
Feb. 5, 2016 (IN) ........................... 3495/CHE/2016
Jun. 28, 2016 (KR) ....................... 10-2016-0081170

(51) Int. Cl.
*A61B 5/103*    (2006.01)
*A61B 5/00*    (2006.01)
(Continued)

(52) U.S. Cl.
CPC .......... *A61B 5/1032* (2013.01); *A61B 5/0077* (2013.01); *A61B 5/1034* (2013.01);
(Continued)

(58) Field of Classification Search
CPC ... A61B 5/1032; A61B 5/0077; A61B 5/1034; A61B 5/441; A61B 5/443; A61B 5/445;
(Continued)

(56) References Cited

U.S. PATENT DOCUMENTS 7,894,651 B2    2/2011 Gutkowicz-Krusin et al.
2004/0213476 A1    10/2004 Luo et al.
(Continued)

FOREIGN PATENT DOCUMENTS

JP    2004-180114    6/2004
JP    2010-520774    6/2010
(Continued)

OTHER PUBLICATIONS

What Is Skin Cancer, Pratt, 2009 https://www.nailsmag.com/article/40762/what-is-skin-cancer (Year: 2009).*
(Continued)

*Primary Examiner* — Jianxun Yang
(74) *Attorney, Agent, or Firm* — The Farrell Law Firm, P.C.

(57) ABSTRACT

Provided are an electronic device and method for providing information related to a skin type of an object. The electronic device includes: a camera configured to capture at least one image including a skin portion and a non-skin portion of an object; and a processor configured to determine at least one color ratio between the skin portion and the non-skin portion from the at least one image, and determine a skin type of the object based on the determined at least one color ratio.

18 Claims, 19 Drawing Sheets

(51) Int. Cl.
*G06T 7/00* (2017.01)
*G06T 7/90* (2017.01)
*H04M 1/725* (2006.01)

(52) U.S. Cl.
CPC .............. *A61B 5/441* (2013.01); *A61B 5/443* (2013.01); *A61B 5/445* (2013.01); *A61B 5/486* (2013.01); *A61B 5/6898* (2013.01); *A61B 5/7264* (2013.01); *A61B 5/743* (2013.01); *G06T 7/0012* (2013.01); *G06T 7/90* (2017.01); *H04M 1/72569* (2013.01); *A61B 5/444* (2013.01); *A61B 5/449* (2013.01); *A61B 2576/00* (2013.01); *G06T 2207/10024* (2013.01); *G06T 2207/30088* (2013.01); *H04M 2250/52* (2013.01)

(58) Field of Classification Search
CPC ..... A61B 5/486; A61B 5/6898; A61B 5/7264; A61B 5/743; A61B 5/444; A61B 5/449; A61B 2576/00; A61B 5/0059; G06T 7/90; G06T 7/0012; G06T 2207/10024; G06T 2207/30088; H04M 1/72569; H04M 2250/52; G06K 9/38; G06Q 30/02; A45D 44/00
See application file for complete search history.

(56) References Cited

U.S. PATENT DOCUMENTS

| | | | |
|---|---|---|---|
| 2006/0265244 A1* | 11/2006 | Baumann | G06Q 30/02 705/2 |
| 2009/0245603 A1* | 10/2009 | Koruga | A45D 44/00 382/128 |
| 2010/0172578 A1 | 7/2010 | Reid et al. | |
| 2010/0309300 A1* | 12/2010 | Chhibber | A61B 5/0059 348/77 |
| 2013/0076932 A1 | 3/2013 | Chhibber et al. | |
| 2014/0177955 A1 | 6/2014 | Srinivasan et al. | |
| 2018/0039864 A1* | 2/2018 | Yao | G06K 9/38 |

FOREIGN PATENT DOCUMENTS

| | | |
|---|---|---|
| KR | 1020120012702 | 2/2012 |
| WO | WO 2013/093851 | 6/2013 |

OTHER PUBLICATIONS

Know Your Skin, Jamie, 2014 https://nursejamie.com/blog/know-skin-begin/ (Year: 2014).*
Fitzpatrick skin phototype, Hon, 2012 https://dermnetnz.org/topics/skin-phototype/ (Year: 2012).*
European Search Report dated May 30, 2018 issued in counterpart application No. 16821624.0-1115, 7 pages.
Ken Hiu-Kan, "Melanonychia", DermNet NZ, https://www.dermnetnz.org/topics/melanonychia/, Jun. 2014, 1 page.
Hardin.MD, "Nail Problems: Picture Gallery", DermNet, http://hardinmd.lib.uiowa.edu/nailspictures2.html, Dec. 15, 2010-Aug. 30, 2017, 1 page.
Fitzpatrick, T.B., "Fitzpatrick Skin Type", http://www.arpansa.gov.au/pubs/RadiationProtection/FitzpatrickSkinType.pdf, 1988, 1 page.
Linkoping University Expanding Reality, "Biomedical Optics Photoacoustics", Department of BioMedical Engineering (IMT), www.liu.se, Jan. 1998, 15 pages.
Romuald Jolivot et al., Skin Parameter Map Retrieval from a Dedicated Mutlispectral Imaging System Applied to Dermatology/Cosmetology, Hindawi Publishing Corp, Research Article, http://www.hindawi.com/journals/ijbi/2013/978289, 2013, 16 pages.
Nikhil Rasiwasia, "Color Space for Skin Detection—A Review", Fondazione Graphitech, University of Trento, (TN) Italy, May 12, 2016, 28 pages.
International Search Report dated Oct. 24, 2016 issued in counterpart application No. PCT/KR20161007260, 17 pages.

* cited by examiner

FIG. 9

| SKIN TYPE | |
|---|---|
| FIRST SKIN TYPE | ~91 |
| VERY EASILY HAS SUNBURN AND IS BARELY TANNED (VERY FAIR SKIN) | |
| SECOND SKIN TYPE | ~92 |
| EASILY HAS SUNBURN AND IS SLIGHTLY TANNED (FAIR SKIN) | |
| THIRD SKIN TYPE | ~93 |
| HAS MEDIUM POSSIBILITIES OF HAVING SUNBURN AND BEING TANNED (LIGHT BROWN SKIN) | |
| FOURTH SKIN TYPE | ~94 |
| OCCASIONALLY HAS SUNBURN AND IS EASILY TANNED (MEDIUM BROWN SKIN) | |
| FIFTH SKIN TYPE | ~95 |
| BARELY HAS SUNBURN AND IS VERY EASILY TANNED (DARK BROWN SKIN) | |
| SIXTH SKIN TYPE | ~96 |
| DOES NOT HAVE SUNBURN (DARK DARK SKIN) | |

FIG. 10

| COLOR RATIO BETWEEN SKIN PORTION OF HAND TO FINGERNAIL PORTION | FIRST SKIN TYPE | SECOND SKIN TYPE | THIRD SKIN TYPE | FOURTH SKIN TYPE | FIFTH SKIN TYPE | SIXTH SKIN TYPE |
|---|---|---|---|---|---|---|
| R | ... | ... | 10.4 | 32.4 | ... | ... |
| G | ... | ... | 3.5 | 2.1 | ... | ... |
| B | ... | ... | 21 | 44.6 | ... | ... |
| H | ... | ... | 79.5 | 43.2 | ... | ... |
| S | ... | ... | 4.8 | 13.9 | ... | ... |
| V | ... | ... | 0.96 | 3.1 | ... | ... |

ELECTRONIC DEVICE AND METHOD FOR PROVIDING INFORMATION RELATED TO SKIN TYPE OF OBJECT

PRIORITY

This application is a National Phase Entry of International Application No. PCT/KR2016/007260 filed on Jul. 5, 2016, claiming priority to Indian Provisional Patent Application No. 3495/CHE/2015 PS filed Jul. 8, 2015, to Indian Complete Patent Application No. 3495/CHE/2015 CS filed Feb. 5, 2016, and to Korean Patent Application No. 10-2016-0081170 filed Jun. 28, 2016, the contents of each of which are incorporated herein by reference.

TECHNICAL FIELD

The present disclosure relates to an electronic device and method for providing information related to a skin type of an object, and more particularly, to an electronic device and method for determining a skin type of an object and providing information related to the skin type.

BACKGROUND ART

Studies on skin types have been generally conducted via clinical trials and tactile determinations. During the clinical trials, a skin type may be determined based on a scoring system (for example, using a Fitzpatrick scale) immediately after visually examining skin. A researcher may provide accumulated scores of each user based on user's responses, and determine a skin type of each user based on the obtained accumulated scores.

For example, in the scoring system, questions may be how often skin is tanned, how often skin is burnt, and how often skin is exposed to ultraviolet (UV) rays. While responding to the questions, the user recalls his/her previous experiences, but since it is difficult to always recall accurate facts, an error may occur in the user's responses.

In this regard, a technique for effectively determining a skin type of a user and providing information related to skin is required.

DETAILED DESCRIPTION OF THE INVENTION

Technical Problem

Provided are an electronic device and method for determining a skin type of an object by distinguishing between a skin portion and a non-skin portion of the object.

Technical Solution

According to an aspect of an embodiment, an electronic device for determining a skin type of an object, the electronic device includes: a camera configured to capture at least one image including a skin portion and a non-skin portion of an object; and a processor configured to determine at least one color ratio between the skin portion and the non-skin portion from the at least one image, and determine a skin type of the object based on the determined at least one color ratio.

The processor may determine at least one skin attribute related to the object, and determine the skin type based on the determined at least one skin attribute and the determined at least one color ratio.

The at least one skin attribute may include at least one of a disease related to the skin portion, a disease related to the non-skin portion, a skin tanning state of the object, and an amount of oily residue on skin of the object.

The processor may determine the at least one color ratio between the skin portion and the non-skin portion according to a plurality of pre-set color elements.

The plurality of pre-set color elements may include at least two of red, green, blue, hue, saturation, and brightness (value) (RGB_HSV).

The non-skin portion may include at least one of a fingernail portion and a conjunctiva portion.

The processor may provide recommendation information for managing skin of the object based on the determined skin type.

The processor may obtain environment information about an environment around the object, and determine the recommendation information based on the environment information and the determined skin type.

The processor may determine the recommendation information based on the environment information, the skin type, and the at least one skin attribute.

The recommendation information may include at least one of information for avoiding sunburn, information about a sunscreen suitable to the object, and information about a recommended length of time for the object to be exposed to sun.

According to an aspect of another embodiment, a method of determining, by an electronic device, a skin type of an object, the method includes: obtaining at least one image including a skin portion and a non-skin portion of an object; determining at least one color ratio between the skin portion and the non-skin portion from the at least one image; and determining a skin type of the object based on the determined at least one skin ratio.

According to an aspect of another embodiment, a computer-readable recording medium has recorded thereon a program which, when executed by a computer, performs the method.

DESCRIPTION OF THE DRAWINGS

FIG. 9 is a diagram of examples of skin types, according to an embodiment.

FIG. 10 is a diagram of an example of a skin type table according to an embodiment.

MODE OF THE INVENTION

Figure 1:
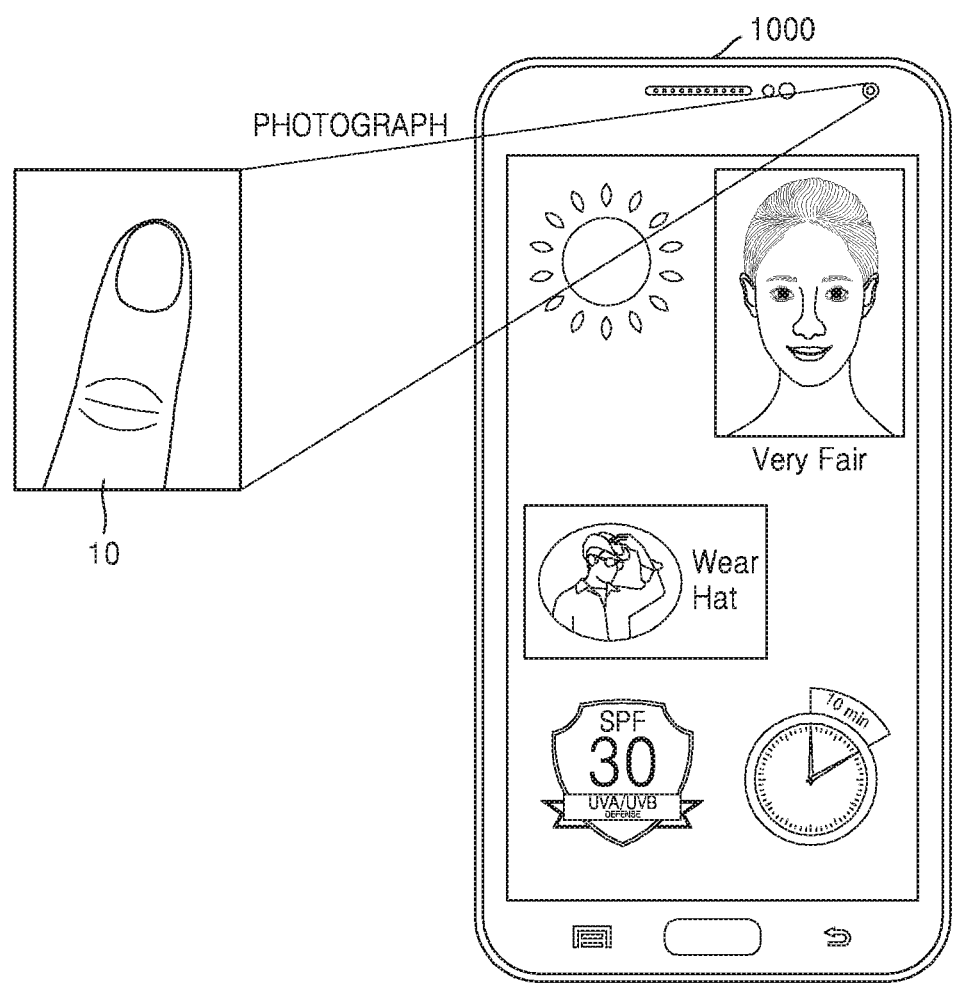
FIG. 1 is a diagram of an example in which an electronic device provides information related to a skin type of an object, according to an embodiment.

One or more embodiments of the present disclosure will now be described more fully with reference to the accompanying drawings. However, the one or more embodiments of the present disclosure may be embodied in many different forms, and should not be construed as being limited to the embodiments set forth herein. Also, in the drawings, elements not related to the description are not shown for clarity of the present disclosure, and like reference numerals denote like or similar elements throughout the specification.

While the terms used in the specification may be used to describe various components, such components must not be limited to the terms. The terms are used only to distinguish one component from another.

Throughout the specification, when a region is "connected" to another region, the regions may not only be "directly connected", but may also be "electrically connected" via another device therebetween. Also, when a region is "connected" to another region, the regions may perform data communication through signal transmission and reception.

Also, when a region "includes" an element, the region may further include another element instead of excluding the other element, otherwise differently stated.

The accompanying drawings may be schematically illustrated to describe one or more embodiments of the present disclosure, and some dimensions may be exaggerated for clarity. Similarly, most parts of the drawings may be arbitrarily represented.

The term "module" used herein may be interpreted as including software, hardware, or a combination thereof based on context of the term. For example, software may be a machine language, firmware, an embedded code, and application software. As another example, hardware may be a circuit, a processor, a computer, an integrated circuit, an integrated circuit core, a sensor, a micro-electro-mechanical system (MEMS), a passive device, or a combination thereof.

The terms used in the specification are merely used to describe particular embodiments, and are not intended to limit the present disclosure. All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the disclosure. Thus, the terms used herein have to be defined based on the meaning of the terms together with the description throughout the specification.

An expression used in the singular encompasses the expression in the plural, unless it has a clearly different meaning in the context. In the present specification, it is to be understood that terms such as "including" or "having", etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The embodiments and the accompanying drawings of the specification are for describing the present disclosure through some of various embodiments of the present disclosure, and the present disclosure is not limited to the embodiments and the accompanying drawings of the specification.

In the embodiments of the present disclosure, the term "object" may denote a user using an electronic device, and for example, a skin type of the object may be determined by using an image of a part of a body or whole body of the object, such as a hand, an eye, or the like of the user.

In the embodiments of the present disclosure, the term "skin type" is a concept for classifying objects having similar skin characteristics together. In general, people of the same race are classified as having the same skin type, but there may be an exception. For example, a skin type may be determined based on a race of an object, a skin color of the object, or the like, but is not limited thereto.

In the embodiments of the present disclosure, the term "skin attribute" may denote a unique attribute related to skin of an object. For example, a skin attribute may include at least one of normal skin, an abnormal fingernail, a skin wound, hyperpigmentation, and hypopigmentation.

Hereinafter, the disclosure will be described in detail with reference to accompanying drawings.

FIG. 1 is a diagram of an example in which an electronic device provides information related to a skin type of an object, according to an embodiment.

As shown in FIG. 1, an electronic device 1000 may image an object, and determine a skin type of the object by analyzing the imaged object. Also, the electronic device 1000 may provide various pieces of recommendation information related to the skin type of the object based on the determined skin type. Recommendation information indicates information that may be beneficially used with respect to skin in daily life of an object of a certain skin type, but a range of the recommendation information is not limited thereto.

For example, the electronic device 1000 may capture an image of a finger 10, i.e., a part of the object, and determine the skin type of the object by analyzing the image of the finger 10. Also, the electronic device 1000 may display, on a screen of the electronic device 1000, for example, information indicating the skin type of the object, information for managing the skin of the object, etc. based on the determined skin type.

Also, the electronic device 1000 may be a smart phone, but this is only an example, and the electronic device 1000 may be realized as various devices including a television (TV), a mobile phone, a tablet personal computer (PC), a digital camera, a camcorder, a laptop computer, a desktop computer, a personal digital assistant (PDA), a portable multimedia player (PMP), a wearable device, etc. The electronic device 1000 according to an embodiment of the present disclosure is not limited to the above devices, and may include a new device according to technical development.

Figure 2:
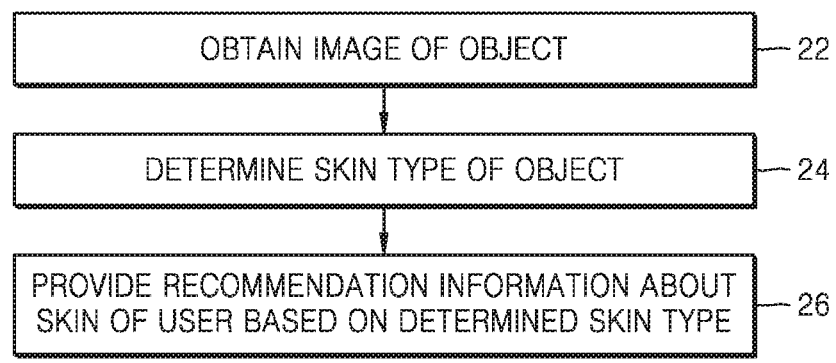
FIG. 2 is a flowchart of a method of operating an electronic device, according to an embodiment.

FIG. 2 is a flowchart of a method of operating an electronic device, according to an embodiment.

In operation 22, the electronic device 1000 may obtain an image of an object. According to an embodiment, the electronic device 1000 may obtain the image of the object by imaging the object using a camera embedded in the electronic device 1000. Alternatively, the electronic device 1000 may receive the image of the object from an external device (not shown) or a server (not shown). In this case, the image of the object may be pre-stored in the external device (not shown) or the server (not shown).

According to an embodiment, the image of the object may include a skin portion and a non-skin portion of the object. The skin portion of the object may be a portion in which an amount of melanin is at a pre-set numerical value or higher, and for example, may include a skin portion of a finger, a skin portion exposed to ultraviolet (UV) rays, a skin portion not exposed to UV rays, etc. Also, for example, the skin portion of the object may be a portion of the object from which the non-skin portion of the object is excluded. The non-skin portion of the object may be a portion in which the amount of melanin is at a pre-set numerical value or lower, and for example, may include a fingernail portion, a toenail portion, a conjunctiva portion, or the like. In operation 24, the electronic device 1000 may determine a skin type of the object. The electronic device 1000 may distinguish the skin portion and the non-skin portion of the object from the image of the object, and determine the skin type of the object based on colors of the skin portion and non-skin portion of the object. At this time, the skin portion of the object and the non-skin portion of the object may be pre-set according to predetermined standards, and information for distinguishing the skin portion of the object and the non-skin portion of the object in the image of the object may be pre-stored in the electronic device 1000.

Also, the electronic device 1000 may determine at least one skin attribute related to the object, and determine the skin type of the object based on the determined at least one skin attribute. In this case, the electronic device 1000 may determine a color ratio between the skin portion and the non-skin portion from the image of the object, and determine the skin type of the object based on the determined at least one skin attribute and the determined color ratio. The skin attribute denotes a unique attribute related to the skin of the object, and for example, may indicate at least one of whether the skin of the object is normal skin, whether a fingernail of the object is a normal fingernail, whether the skin of the object has a wound, whether the skin of the object has hyperpigmentation, and whether the skin of the object has hypopigmentation.

In operation 26, the electronic device 1000 may provide recommendation information related to the skin of the user based on the determined skin type. The recommendation information related to the skin may include, for example, information indicating the skin type and information for managing the skin. According to an embodiment, the recommendation information related to the skin of the user may include, for example, at least one of recommendation behavior information indicating behavior of the user for protecting the skin, sunscreen-related information related to a sunscreen related to be applied to the skin, and information about a UV-exposable time for protecting the skin.

Figure 3:
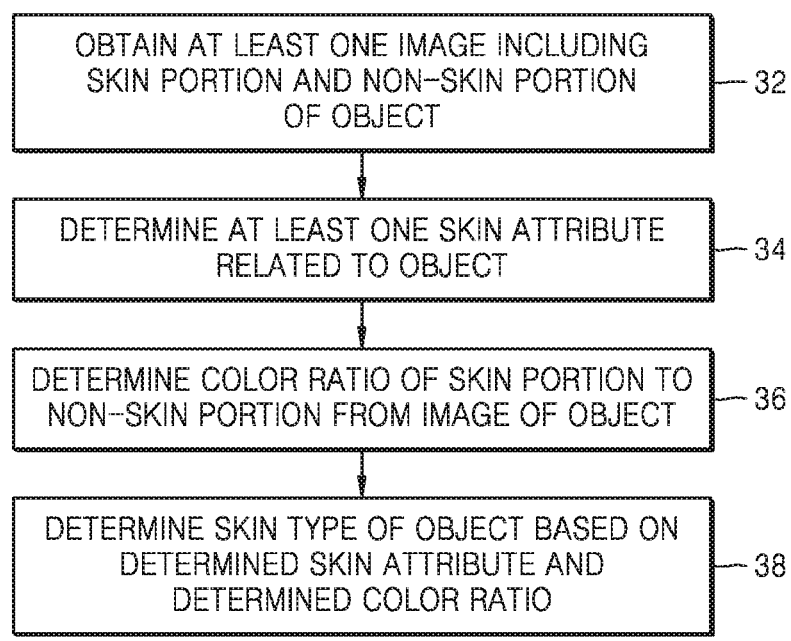
FIG. 3 is a flowchart of a method of determining, by an electronic device, a skin type of an object, according to an embodiment.

FIG. 3 is a flowchart of a method of determining, by an electronic device, a skin type of an object, according to an embodiment.

In operation 32, the electronic device 1000 may obtain at least one image including a skin portion and a non-skin portion of an object. The electronic device 1000 may obtain the image of the object by imaging the object using the camera embedded in the electronic device 1000. Alternatively, the electronic device 1000 may receive the image of the object from an external device (not shown) or a server (not shown).

In operation 34, the electronic device 1000 may determine at least one skin attribute related to the object. The skin attribute denotes a unique attribute related to skin of the object, and for example, may indicate at least one of whether the skin of the object is normal skin, whether a fingernail of the object is a normal fingernail, whether the skin of the object has a wound, whether the skin of the object has hyperpigmentation, and whether the skin of the object has hypopigmentation.

The electronic device 1000 may determine the skin attribute of the object by analyzing the image of the object. In this case, the electronic device 1000 may pre-store information about various skin attributes, and may determine the skin attribute of the object from the image of the object by using the pre-stored information about skin attributes.

For example, the electronic device 1000 may pre-store information indicating that the skin attribute of the object corresponds to an abnormal fingernail when albedo of the fingernail is outside a pre-set albedo value range. Also, for example, the electronic device 1000 may determine whether the albedo of the fingernail is outside the pre-set albedo range from the image of the object, and determine whether the fingernail of the object is abnormal.

Also, information about skin attributes may be stored in a server (not shown), wherein the electronic device 1000 may receive the information about skin attributes from the server (not shown) and determine the skin attribute of the object by using the received information about skin attributes. Alternatively, the electronic device 1000 may provide the image of the object to the server (not shown), and request the server (not shown) to determine the skin attribute of the object.

In operation 36, the electronic device 1000 may determine a color ratio of the skin portion to the non-skin portion from the image of the object.

According to an embodiment, the color ratio of the skin portion to the non-skin portion may be, for example, ratios of RGB-HSV values. R may denote red, G may denote green, blue may denote blue, H may denote hue, S may denote saturation, and V may denote a brightness value.

According to an embodiment, the color ratio of the skin portion to the non-skin portion may be determined by using Equation 1 below.

$$\text{Color Ratio} = \frac{I*(\text{Albedo of Skin Portion})}{I*(\text{Albedo of Non-Skin Portion})} = \frac{\text{Albedo of Skin Portion}}{\text{Albedo of Non-Skin Portion}} \quad [\text{Equation 1}]$$

In Equation 1, I denotes an illumination factor.

According to an embodiment, an illumination factor may be, for example, a parameter in which a measurement of an individual characteristic, an environmental factor, etc. affecting brightness of the image of the object is represented as a numerical value. For example, at least one of a lighting condition, a skin tanning state, and an amount of oily residues on the skin.

For example, a numerical value of the illumination factor I may be high when the skin of the object is not tanned, the amount of oily residues on the skin of the object is large, and current lighting is bright.

Referring to Equation 1, since the illumination factors I in the denominator and the numerator canceled each other out, the color ratio may be obtained by dividing the albedo of the skin portion by the albedo of the non-skin portion. The electronic device 1000 may calculate the color ratio of the skin portion to the non-skin portion without considering the illumination factor I.

According to an embodiment, a characteristic vector of the color ratio may be represented as Equation 2 below. The characteristic vector of the color ratio may be used by the electronic device 1000 to determine the skin type of the object by using a skin type table.

$$<R(s)/R(n), G(s)/G(n), B(s)/B(n), H(s)/H(n), S(s)/S(n), V(s)/V(n)> \quad \text{[Equation 2]}$$

In Equation 2, s denotes a parameter of the skin portion of the object and n denotes a parameter of the non-skin portion.

According to an embodiment, the electronic device 1000 may calculate a K-vector (R, G, B, H, S, V, X, X, X) based on the characteristic vector of the color ratio of Equation 2. In the K-vector, 6 left 6 components are the characteristic vector of the color ratio and the right 3 components denote non-color characteristics.

In operation 38, the electronic device 1000 may determine the skin type of the object based on the determined skin attribute and the determined color ratio.

According to an embodiment, the electronic device 1000 may detect a value closest to the determined color ratio of the object from the skin type table based on the determined skin attribute and the determined color ratio, and determine the skin type of the object based on a detected result.

According to an embodiment, a skin type table corresponding to a skin attribute may exist for each skin attribute related to an object. For example, a skin type table when the skin attribute of the object is normal skin, a skin type table when the skin attribute of the object is an abnormal fingernail, and a skin type table when the skin attribute of the object is hyperpigmentation may independently exist. Also, the electronic device 1000 may extract the skin type table corresponding to the skin attribute of the object according to the skin attribute of the object, and determine the skin type of the object by using the extracted skin type table.

Alternatively, a parameter corresponding to at least one skin attribute related to the object may exist. The parameter corresponding to at least one skin attribute related to the object may affect the color ratio of the skin portion to the non-skin portion. For example, only one skin type table may exist regardless of the at least one skin attribute related to the object, and the parameter corresponding to the at least one skin attribute related to the object may exist to affect the color ratio of the skin portion of the object to the non-skin portion. In this case, the electronic device 1000 may calculate the color ratio compensated for according to the skin attribute by using the parameter corresponding to the skin attribute, and determine the skin type of the object by using the compensated color ratio and the skin type table.

Figure 4:
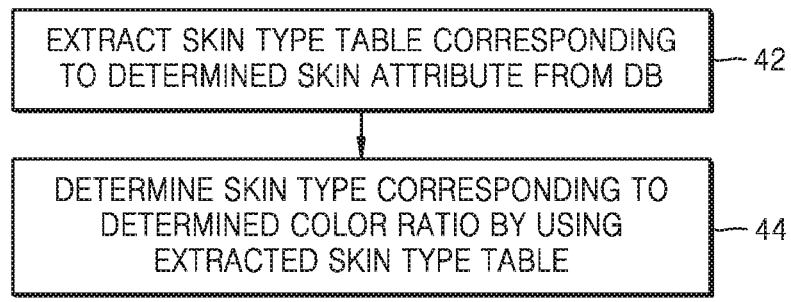
FIG. 4 is a flowchart of a method of determining, by an electronic device, a skin type of an object by using a skin type table, according to an embodiment.

FIG. 4 is a flowchart of a method of determining, by the electronic device 1000, a skin type of an object by using a skin type table, according to an embodiment.

In operation 42, the electronic device 1000 may extract a skin type table corresponding to a determined skin attribute from a database (DB).

For example, when the determined skin attribute is an 'abnormal fingernail', the electronic device 1000 may extract a skin type table corresponding to the abnormal fingernail from the DB.

In operation 42, it is described that a skin type table corresponding to a skin attribute exists according to skin attributes, but one skin type table may be used regardless of a skin attribute so as to determine a skin type. For example, when the skin attribute is determined to be the 'abnormal fingernail', a parameter corresponding to the 'abnormal fingernail' may be determined and the determined parameter may affect a color ratio of a skin portion to a non-skin portion.

According to an embodiment, a value of the parameter (a parameter value) that may affect the color ratio of the skin portion to the non-skin portion may vary according to, for example, a race of the object, area proportions of the skin portion and the non-skin portion of the object in the image, a current time, a current weather, a current location, an image of a surrounding environment of the object, a characteristic of the image including the skin portion and the non-skin portion of the object (for example, a type, pixel, or the like of the image), and a survey result of the object.

For example, the electronic device 1000 may determine whether the object is currently directly exposed to UV rays of the sun based on global positioning system (GPS) data, an image of a sky around the object, and weather information, and a determination result may change the value of the parameter that may affect the color ratio of the skin portion to the non-skin portion.

In operation 44, the electronic device 1000 may determine a skin type corresponding to the determined color ratio by using the extracted skin type table.

When a skin type table exists per skin attribute, the electronic device 1000 may compare the color ratio of the object and the skin type table by using the skin type table corresponding to the skin attribute. Also, the electronic device 1000 may determine, as the skin type of the object, a skin type having a color ratio most similar to the color ratio of the object.

Alternatively, when one skin type table exists regardless of the skin attribute of the object, the electronic device 1000 may compensate for the color ratio by using the parameter corresponding to the skin attribute, and determine the skin type of the object by using the compensated color ratio and the skin type table. Alternatively, the electronic device 1000 may calculate the color ratio to which the skin attribute is reflected by using the parameter corresponding to the skin attribute, and determine the skin type of the object by using the calculated color ratio and the skin type table.

Figure 5:
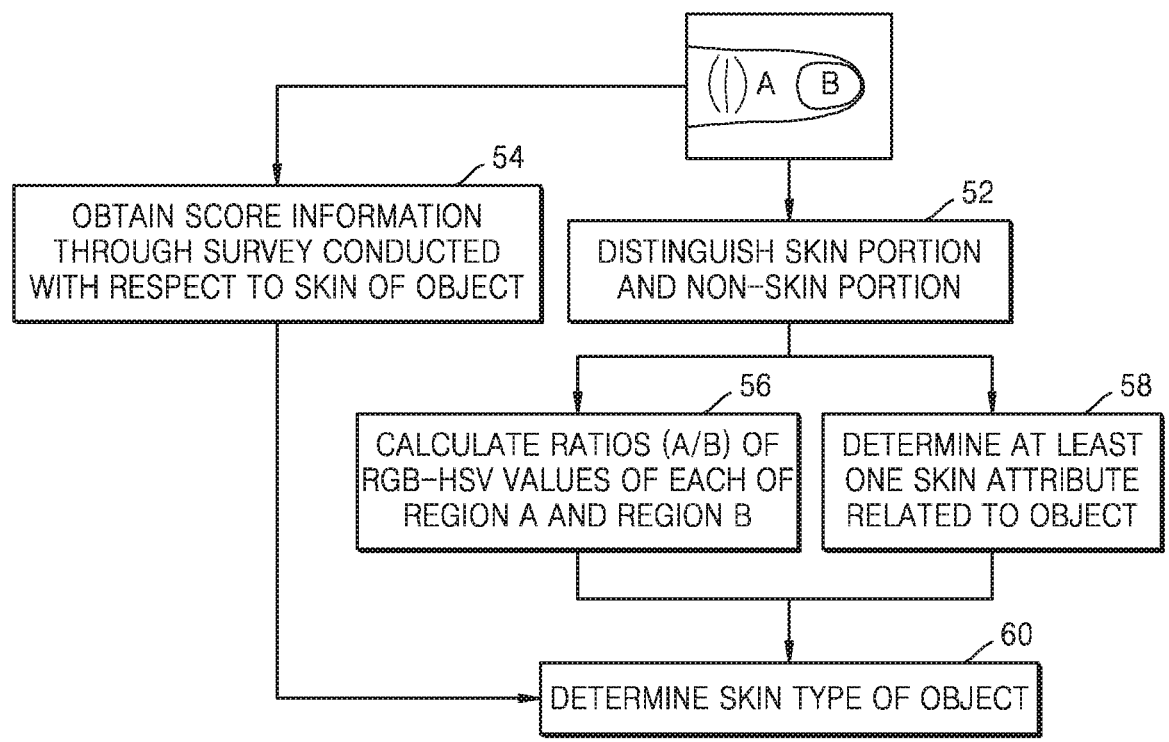
FIG. 5 is a flowchart of a method of determining, by an electronic device, a skin type of an object by using information about scores from a survey, according to an embodiment.

FIG. 5 is a flowchart of a method of determining, by an electronic device, a skin type of an object by using score information through a survey, according to an embodiment.

In operation 52, the electronic device 1000 may distinguish a skin portion A and a non-skin portion B from at least one image including a skin portion and a non-skin portion of an object.

According to an embodiment, the electronic device 1000 may pre-store information for distinguishing the skin portion A and the non-skin portion B. The electronic device 1000 may distinguish the skin portion A and the non-skin portion B from the image of the object by using the pre-stored information for distinguishing the skin portion A and the non-skin portion B.

For example, the electronic device 1000 may pre-store information about various fingernail shapes. When a fingernail shape is detected from the image, the electronic device 1000 may determine a region corresponding to the fingernail shape as the non-skin portion and a remaining region as the skin portion A.

In operation 54, the electronic device 1000 may obtain score information through a survey conducted with respect to skin of the object. In order to obtain the information about the skin of the object, the electronic device 1000 may display, on a screen of the electronic device 1000, a survey about the skin of the object. Also, the electronic device 1000 may obtain the information about the skin of the object based on a user input responding to the survey, and assign a score per item of the survey based on a predetermined standard.

For example, the electronic device 1000 may display, on the screen of the electronic device 1000, text for asking 'how often have you burnt your skin?', 'how often is your skin exposed to UV rays?', 'what is the average UV exposure time?', etc.

Alternatively, according to an embodiment, a predetermined sensor may be attached to the skin of the object, and the electronic device 1000 may receive the information about the skin of the object from the sensor. For example, the sensor attached to the object may sense a number of times and a time the object is exposed to UV rays, and transmit sensed values to the electronic device 1000. Also, the electronic device 1000 may analyze, for example, 'how often have you burnt your skin', 'how often is your skin exposed to UV rays', 'what is the average UV exposure time', etc., and assign a predetermined score per pre-set item about the skin.

The electronic device 1000 may use at least some of the obtained score information to generate a skin type table, but is not limited thereto.

Also, a survey result about the skin of the object may be provided to a server (not shown), and the server (not shown) may generate a skin type table based on survey results about the skin of a plurality of objects. In this case, the survey about the skin of the object may include various questions, for example, for determining a color ratio, etc. according to a skin type of a skin type table, but is not limited thereto. Also, the server (not shown) may categorize the skin into six different types (a first type to a sixth type) according to a degree of pigmentation of the skin by using a scoring system based on the survey. Also, a skin type table generated by the server (not shown) may be provided to the electronic device 1000.

In operation 56, the electronic device 1000 calculates ratios (A/B) of RGB-HSV values of each of the region A and the region B, and in operation 58, the electronic device 1000 may determine at least one skin attribute related to the object. The electronic device 1000 may determine the skin attribute of the object by using at least some of the score information obtained in operation 54, but is not limited thereto.

In operation 60, the electronic device 1000 may determine a skin type of the object. The electronic device 1000 may detect a value closest to the determined color ratio of the object from the skin type table based on the skin attribute determined in operation 58 and the color ratio determined in operation 56, and determine the skin type of the object based on a detected result.

Figure 6:
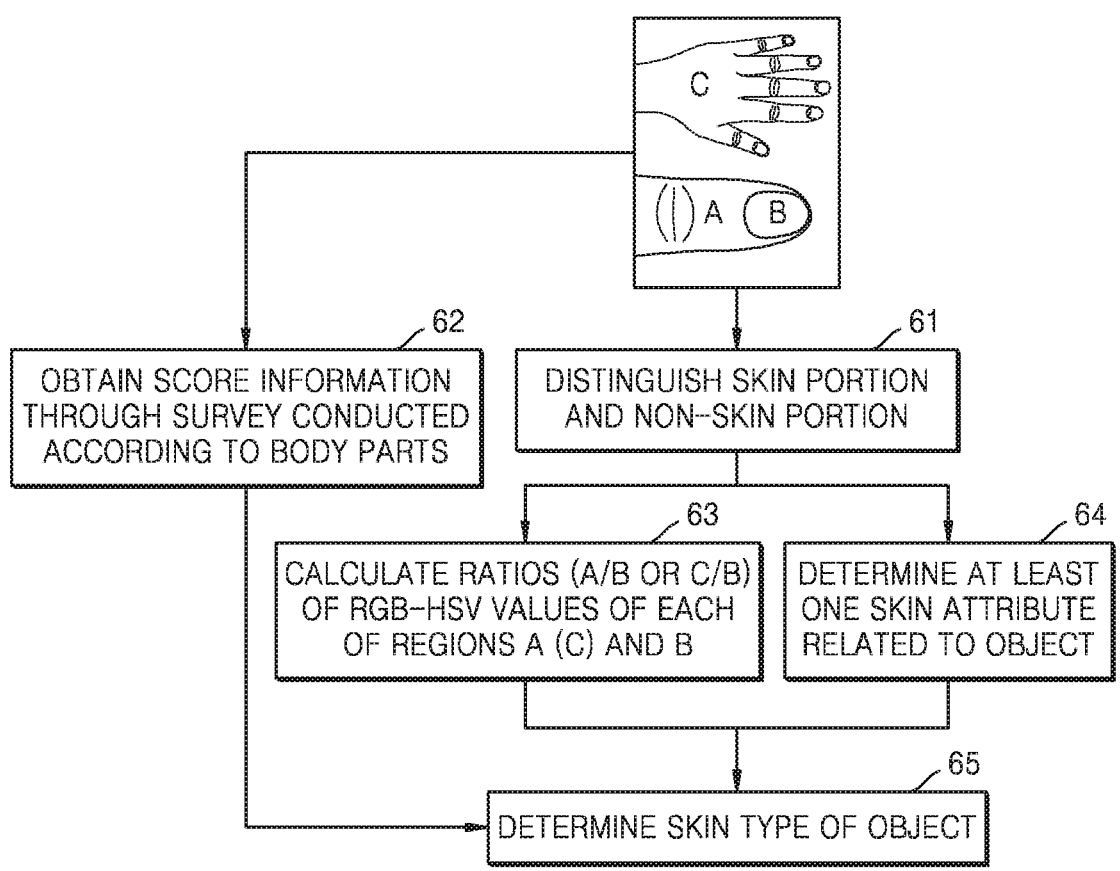
FIG. 6 is a flowchart of a method of determining a skin type based on a survey conducted according to body parts of an object, according to an embodiment.

FIG. 6 is a flowchart of a method of determining a skin type based on a survey conducted according to body parts of an object, according to an embodiment.

In operation 61, the electronic device 1000 may distinguish the skin portion A and the non-skin portion B from at least one image including the skin portion A and the non-skin portion B of an object.

In operation 62, the electronic device 1000 may obtain score information through a survey conducted according to body parts of the object. In order to obtain information about skin of the object, the electronic device 1000 may display, on a screen of the electronic device 1000, a survey about the skin according to body parts. Also, the electronic device 1000 may obtain the information about the skin according to body parts of the object based on a user input responding to the survey, and assign a score per item of the survey according to a predetermined standard.

In operation 63, the electronic device 1000 may calculate ratios (A (or C)/B) of RGB-HSV values of each of the regions A (or C) and B, and in operation 64, the electronic device 1000 may determine at least one skin attribute related to the object. In operation 63, the region C corresponds to another skin portion (back of a hand) excluding a finger portion. As shown in operation 63, a skin type of the object may be detected not only by analyzing one image, but also by analyzing two or more images.

For example, as shown in FIG. 6, the electronic device 1000 may obtain a first image including the regions A and B, and a second image including the region C. The electronic device 1000 may determine the region B in the first image as a non-skin portion and the region C in the second image as a skin portion, and calculate a color ratio (C/B) according to RGB-HSV values of each of the regions C and B. Also, the electronic device 1000 may determine the region B in the first image as a non-skin portion and the region A in the first image as a skin portion, and calculate a color ratio (A/B) according to RGB-HSV values of each of the regions A and B.

In operation 65, the electronic device 1000 may determine the skin type of the object.

The electronic device 1000 may detect a value closest to the determined color ratio of the object form the skin type table based on the skin attribute determined in operation 65 and the color ratio determined in operation 63, and determine the skin type of the object based on a detected result. The electronic device 1000 may, for example, calculate an average value of a plurality of color ratios determined in operation 63, and determine the skin type of the object from the skin type table by using the calculated average value, but is not limited thereto.

Figure 7A:
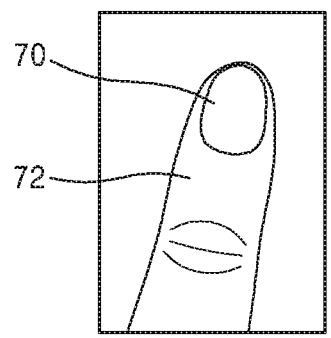
FIGS. 7A and 7B are diagrams of examples of skin portions and non-skin portions of an object, according to an embodiment.
Figure 7B:
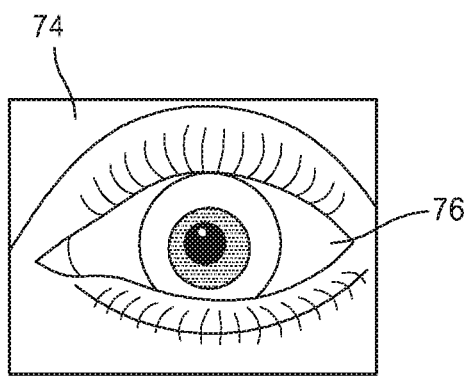

FIGS. 7A and 7B are diagrams of examples of skin portions and non-skin portions of an object, according to an embodiment.

According to an embodiment, a skin portion of an object may include all skin portions of the object including a portion having abundant melanin in skin, a phalange, a skin portion exposed to UV rays, a skin portion not exposed to UV rays, etc.

According to an embodiment, a non-skin portion of an object may denote a portion having insufficient melanin in skin, a fingernail portion, a toenail portion, conjunctiva, or the like.

A fingernail portion of the object may include, for example, pure keratin, and may not include melanin or have pigmentation.

Referring to FIG. 7A, a fingernail image may be distinguished into a skin portion 72 and a non-skin portion 70. According to an embodiment, the electronic device 1000 may calculate a color ratio of the skin portion 72 to the non-skin portion 70, and determine a skin type of an object based on the calculated color ratio.

Referring to FIG. 7B, an eye image may be distinguished into a skin portion 74 and a non-skin conjunctiva portion 76. According to an embodiment, the electronic device 1000 may calculate a color ratio of the skin portion 74 to the non-skin conjunctiva portion 76, and determine a skin type of an object based on the calculated color ratio.

Figure 8:
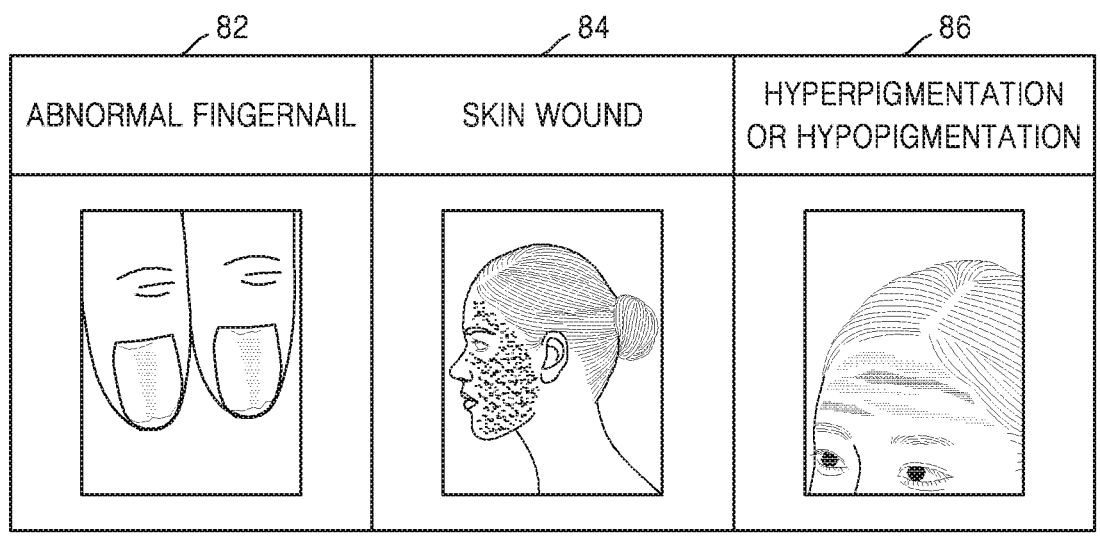
FIG. 8 is a diagram of examples of skin attributes, according to an embodiment.

FIG. 8 is a diagram of examples of skin attributes, according to an embodiment.

According to an embodiment, skin attributes may include at least one of an abnormal fingernail 82, a skin wound 84, and hyperpigmentation or hypopigmentation 86.

For example, when a fingernail is bluish or white, the fingernail of an object may correspond to the abnormal fingernail 82. When the fingernail of the object corresponds to the abnormal fingernail 82, albedo of a fingernail portion may be different from that when a fingernail is normal, and thus a color ratio of a skin portion to a non-skin portion may also be different.

According to an embodiment, the skin wound 84 may include a burn, an injury, a sting, etc. When a skin attribute of the object corresponds to the skin wound 84, albedo of a skin portion may be different from that when the skin is normal, and thus a color ratio of the skin portion to a non-skin portion may also be different.

Also, since skin of a child under the age of 10 is sensitive skin having thinner epidermis than an adult and having low melanin, the skin of the child under the age of 10 may be classified as an independent skin attribute different from skin of a person aged 10 or older.

According to an embodiment, the electronic device 1000 may use a skin type table corresponding to a skin attribute, according to skin attributes. For example, when the skin attribute is the abnormal fingernail 82, the electronic device 1000 may extract, from a DB, a skin type table corresponding to the abnormal fingernail 82, and determine a skin type of the object based on the extracted skin type table.

According to an embodiment, the electronic device 1000 may automatically determine a type of the skin attribute of the object by analyzing an image regarding the object. For example, a shape and color of the object image, a survey result, etc. may be used in order to automatically determine the type of the skin attribute of the object.

FIG. 9 is a diagram of examples of a skin type, according to an embodiment.

FIG. 9 is only an embodiment of classifying skin types, and the classified skin types are not limited by the embodiment of FIG. 9. Also, characteristics of each skin type shown in FIG. 9 are also only examples, and are not limited by the embodiment of FIG. 9.

According to an embodiment, very fair skin may be classified as a first skin type 91. The first skin type very easily has sunburn and is barely tanned.

According to an embodiment, fair skin may be classified as a second skin type 92. The second skin type easily has sunburn and is slightly tanned.

According to an embodiment, light brown skin may be classified as a third skin type 93. The third skin type has medium possibilities of having sunburn and being tanned.

According to an embodiment, medium brown skin may be classified as a fourth skin type 94. The fourth skin type occasionally has sunburn and is easily tanned.

According to an embodiment, dark brown skin may be classified as a fifth skin type 95. The fifth skin type barely has sunburn and is very easily tanned.

According to an embodiment, dark dark skin may be classified as a sixth skin type 96. The sixth skin type does not have sunburn.

FIG. 10 is a diagram of an example of a skin type table according to an embodiment.

The skin type table of FIG. 10 shows color ratios of skin portions of hands to fingernail portions when skin types are third and fourth skin types.

Referring to FIG. 10, the color ratios of the skin portions of the hands to the fingernail portions may be recorded in the skin type table according to RGB-HSV values. The electronic device 1000 may determine a skin type of an object by comparing color ratios of the object calculated according to RGB-HSV values with the color ratios recorded in the skin type table. For example, when the color ratios of the object according to RGB-HSV values have values between the color ratios of the third skin type and the color ratios of the fourth skin type, the electronic device 1000 may determine the skin type of the object based on similarity between the color ratios of the object and the color ratios of the third skin type and similarity between the color ratios of the object and the color ratios of the fourth skin type.

Also, for example, differences between the color ratio values when a skin type is the third skin type and the color ratio values when a skin type is the fourth skin type may be large, and in this case, the skin type of the object may be more clearly determined.

According to an embodiment, since a skin type table corresponding to a skin attribute may vary according to a skin attribute of an object, numerical values in a skin type table may also vary when a skin attribute is varied.

Figure 11:
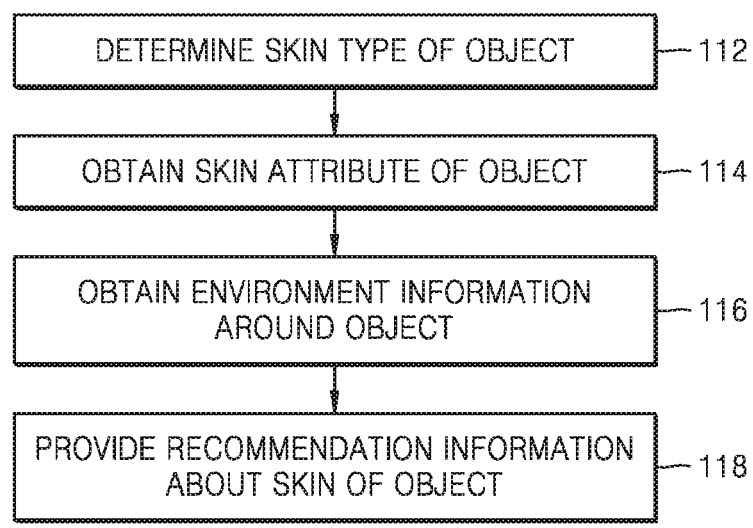
FIG. 11 is a flowchart of a method of providing recommendation information related to skin of an object, according to an embodiment.

FIG. 11 is a flowchart of a method of providing recommendation information related to skin of an object, according to an embodiment.

In operation 112, the electronic device 1000 may determine a skin type of an object, and in operation 114, the electronic device 1000 may obtain a skin attribute of the object.

In operation 116, the electronic device 1000 may obtain environment information around the object. According to an embodiment, the environment information may include a current time, a current location, whether a lighting system exists in an object surrounding environment, whether the object is directly exposed to the sun, etc.

The electronic device 1000 may obtain the environment information around the object by using a sensor embedded in the electronic device 1000. The electronic device 1000 may obtain the environment information by, for example, measuring a position of the electronic device 1000 by using a GPS sensor and measuring surrounding brightness by using an illumination sensor, but is not limited thereto.

In operation 118, the electronic device 1000 may provide recommendation information about the skin of the object. The electronic device 1000 may obtain the recommendation information for managing the skin of the object by using at least one of the skin type, the skin attribute, and the environment information of the object.

According to an embodiment, the electronic device 1000 may determine the recommendation information about the skin of the object based on the obtained environment information. For example, when environment information that current weather is clear with strong UV rays and the object is currently directly exposed to UV rays is obtained, the electronic device 1000 may determine the recommendation information to recommending the object to "enter a building to avoid UV rays", and "if exposure to UV rays is inevitable, apply a sunscreen and wear a hat and sunglasses". Also, the electronic device 1000 may obtain the recommendation information to be provided to the user by using the skin attribute.

For example, the electronic device 1000 may determine skin cancer occurrence possibility of the object by using the determined skin type, skin attribute, and environment information. The electronic device 1000 may display, on a screen of the electronic device 1000, the determined skin cancer occurrence possibility. Also, the electronic device 1000 may display, on the screen of the electronic device 1000, information for preventing skin cancer occurrence.

Also, for example, the electronic device 1000 may determine a skin malignant melanoma occurrence possibility of the object by using the determined skin type, skin attribute, and environment information. The electronic device 1000 may display the determined skin malignant melanoma occurrence possibility. Also, the electronic device 1000 may display, on the screen of the electronic device 1000, information for preventing skin malignant melanoma occurrence.

Also, the recommendation information may include at least one of, for example, information about a behavior recommended to the object, sunscreen-related information, and information about a UV exposable time. Examples of the recommendation information about the skin of the object and details thereof will be described below with reference to FIG. 14.

Figure 12:
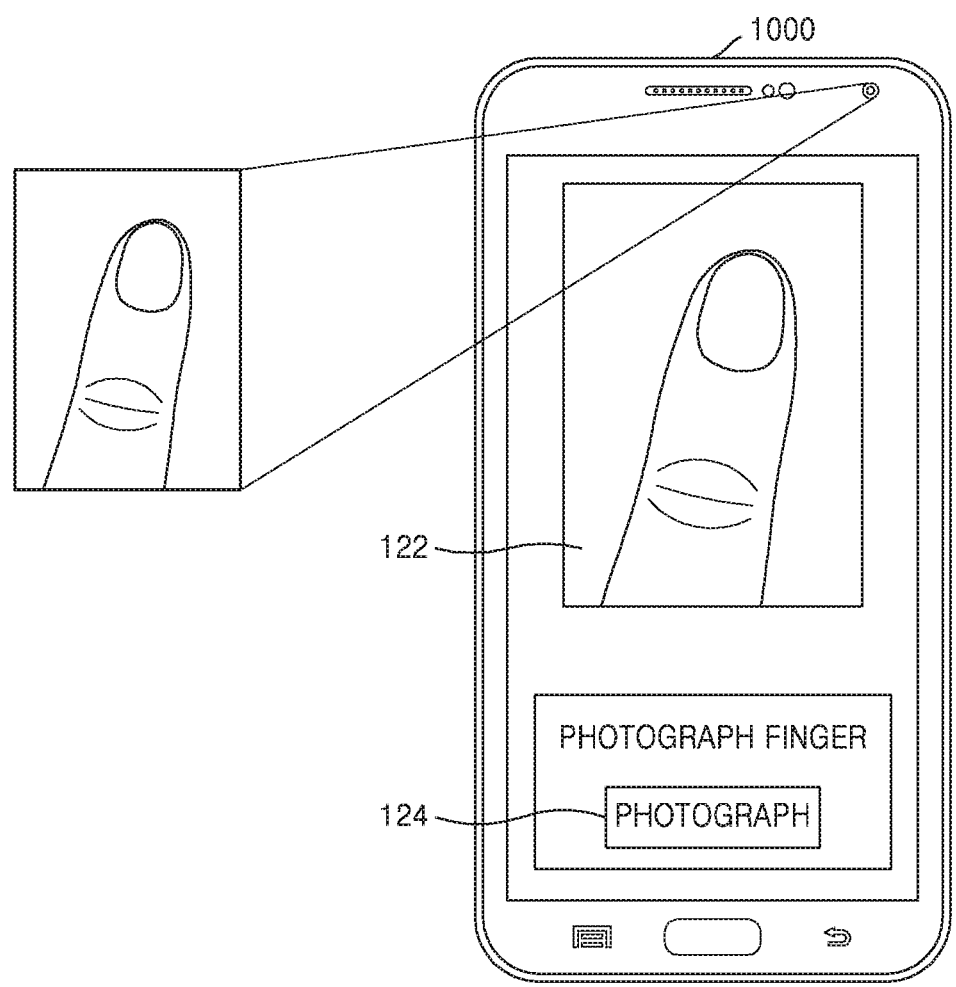
FIG. 12 is a diagram of an example of obtaining an image of a part of a body of an object, according to an embodiment.

FIG. 12 is a diagram of an example of obtaining an image of a part of a body of an object, according to an embodiment.

According to an embodiment, the electronic device 1000 may transmit a popup message to an object so as to obtain at least one image including a skin portion and a non-skin portion of the object. For example, as shown in FIG. 12, the electronic device 1000 may display a popup message including a phrase "please photograph a finger" so that the object may display, on a screen of the electronic device 1000, a graphical user interface (GUI) for capturing at least one image including a skin portion and a non-skin portion.

Also, for example, when the user touches an imaging button 124 on a display screen of the electronic device 1000, the electronic device 1000 may image a finger of the user.

Figure 13A:
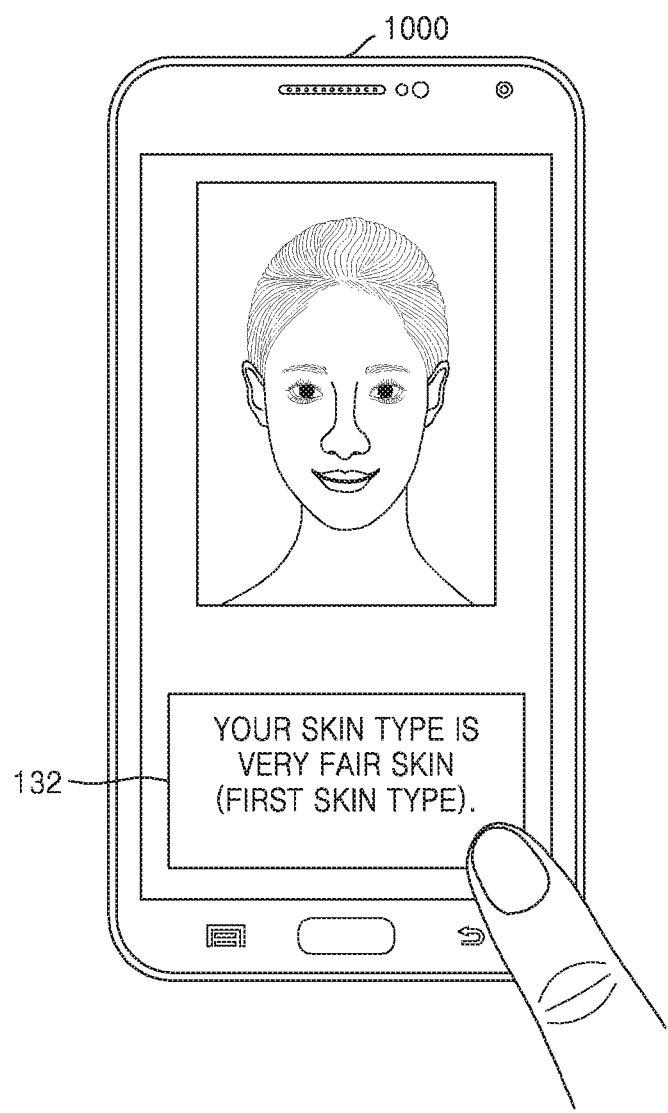
FIGS. 13A and 13B are diagrams of an example of a screen of an electronic device displaying information related to a skin type of an object, according to an embodiment.
Figure 13B:
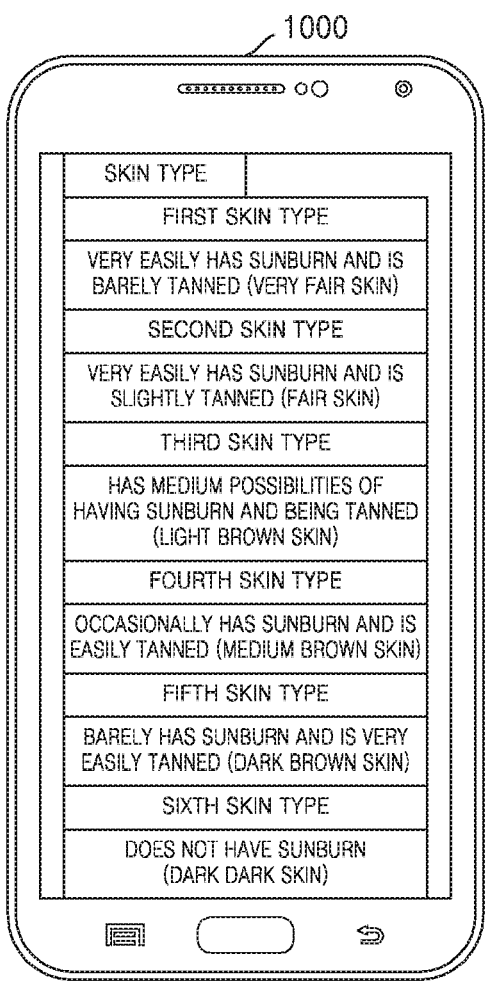

FIGS. 13A and 13B are diagrams of an example of a screen of an electronic device displaying information related to a skin type of an object, according to an embodiment.

As shown in FIG. 13A, when a skin type of an object is determined to be, for example, a first skin type, the electronic device 1000 may display a phrase 132 "your skin type is very fair skin (first skin type)".

According to an embodiment, when a user of the electronic device 1000 touches the phrase 132 displayed on the electronic device 1000, detailed information about the skin type may be displayed as shown in FIG. 13B.

According to an embodiment, when the user is doubtful about the determined skin type, the user may enable the electronic device 1000 to determine the skin type again. In this case, the electronic device 1000 may repeat a series of processes for determining the skin type of the object, and determine the skin type of the object again.

Figure 14:
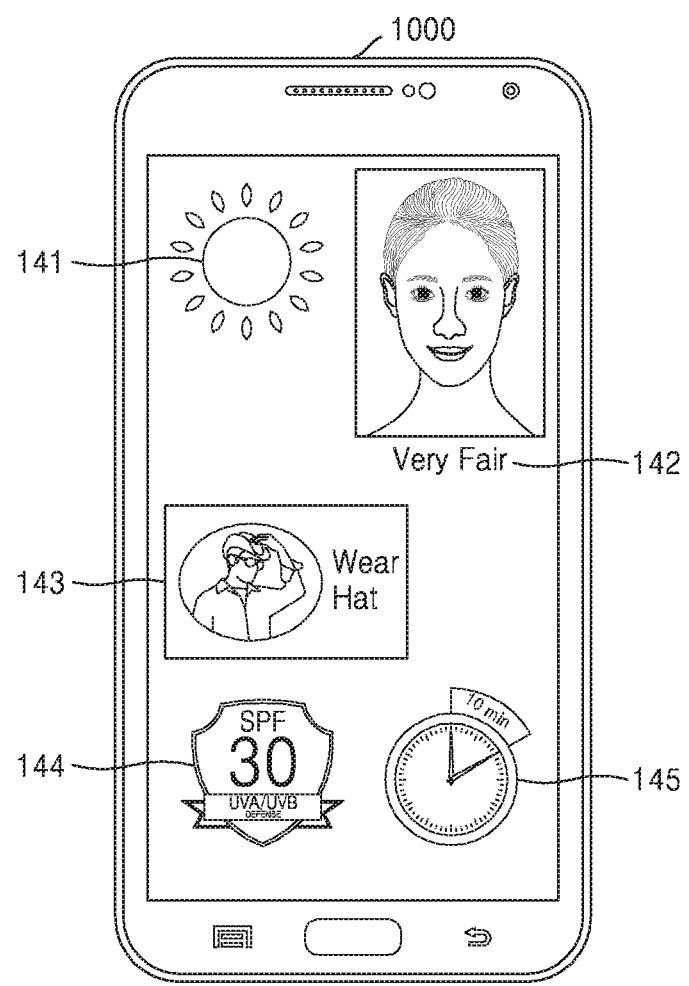
FIG. 14 is a diagram of an example of displaying recommendation information related to skin of an object, according to an embodiment.

FIG. 14 is a diagram of an example of displaying recommendation information related to skin of an object, according to an embodiment.

According to an embodiment, the electronic device 1000 may display current weather information 141.

For example, as shown in FIG. 14, when current weather is clear, the electronic device 1000 may display an image 141 of the sun. Also, when the image 141 is selected by a user, current detail weather may be displayed on a screen of the electronic device 1000.

According to an embodiment, the electronic device 1000 may display text 142 indicating a skin type of an object. Also, when the text 142 is selected by the user, detail information about the skin type of the object may be displayed on the screen of the electronic device 1000.

According to an embodiment, the electronic device 1000 may display recommendation behavior information of the object. The electronic device 1000 may display, on the screen of the electronic device 1000, an image 143 indicating recommended behavior conducted by the user to protect skin. Also, when the image 143 is selected by the user, detailed information to be conducted by the user to protect the skin may be displayed on the screen of the electronic device 1000.

The image 143 indicating the recommendation behavior information may include a phrase, such as wear hat, find shade, wear sunglasses, or the like, but is not limited thereto.

For example, when the current weather has strong UV rays, the electronic device 1000 may recommend the object to wear a hat, find a shade, and wear sunglasses.

According to an embodiment, the electronic device 1000 may display sunscreen-related information. The electronic device 1000 may display, on the screen of the electronic device 1000, an image 144 indicating a type of a sunscreen to be used by the user to protect the skin. For example, the electronic device 1000 may display information indicating that a sunscreen having a sun protection factor (SPF) of 30 with respect to UVA and SPF of 50 with respect to UVB is most efficient. Also, when the user selects the image 144, a recommended list for purchasing a sunscreen may be displayed on the screen of the electronic device 1000.

Also, the electronic device 1000 may display information about progression of skin cancer (melanoma) of the object.

For example, when the progression of skin cancer (melanoma) of the object exceeds risk level, the electronic device 1000 may recommend information indicating that the object is required to avoid going out for at least 10 days.

According to an embodiment, the electronic device 1000 may display information about a UV exposable time.

For example, when it is determined that a possibility of the object having sunburn is remote even when the object is directly exposed to UV rays for 10 minutes, the electronic device 1000 may display, on the screen of the electronic device 1000, an image 145 indicating information that the object is exposable to UV rays for 10 minutes.

According to an embodiment, a period of time in which the object is exposable to UV rays may vary according to a current UV index. For example, a UV exposable time of the object may be lower than usual when a UV index is higher than usual.

Figure 15:
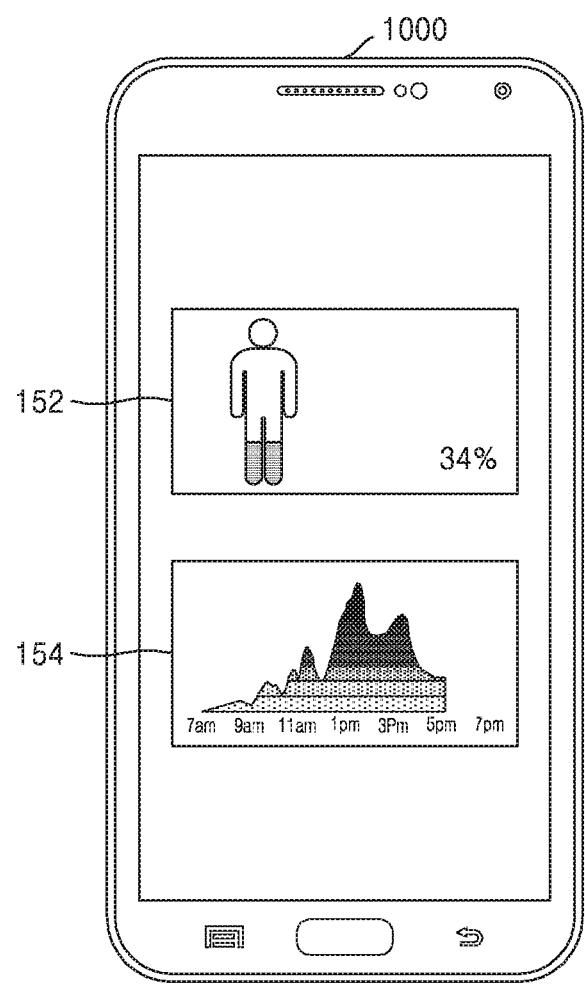
FIG. 15 is a diagram of an example in which an electronic device displays an ultraviolet (UV) exposure dose of an object, according to an embodiment.

FIG. 15 is a diagram of an example in which an electronic device displays a UV exposure dose of an object, according to an embodiment.

According to an embodiment, the electronic device 1000 may display information 152 indicating a ratio of a minimal UV exposure dose that may cause an object to have erythema to a current UV exposure dose.

The minimal UV exposure dose that may cause the object to have erythema is referred to as a minimal erythema dose (MED). Examining MED per skin type, for example, a first skin type may be 20 to 35, a second skin type may be 30 to 45, a third skin type may be 40 to 55, a fourth skin type may be 50 to 80, a fifth skin type may be 70 to 100, and a sixth skin type may be 100, wherein the MED may be in units of $J/cm^2$. Also, the electronic device 1000 may monitor an exposure dose of the object exposed to UV rays by using, for example, a sensor (not shown) attached to the object, but is not limited thereto.

According to an embodiment, the electronic device 1000 may display a graph 154 indicating a UV exposure dose of the object according to time. In the graph 154 indicating the UV exposure dose of the object according to time, an area below the graph may indicate an accumulated exposure dose of the object exposed to UV rays for a day.

According to an embodiment, when the electronic device 1000 finds uniqueness in relation to skin of the object while performing at least some of functions of the electronic device 1000 described with reference to FIGS. 1 through 15, the electronic device 1000 may output a notification. Alternatively, the electronic device 1000 may stimulate at least one of senses of sight, hearing, and touch of the object to notify the object that an allowable UV exposure dose is exceeded.

For example, when a UV exposure dose for a certain period of time exceeds a pre-set allowable UV exposure dose after analyzing the UV exposure dose of the object according to time, the electronic device 1000 may output a notification.

Figure 16:
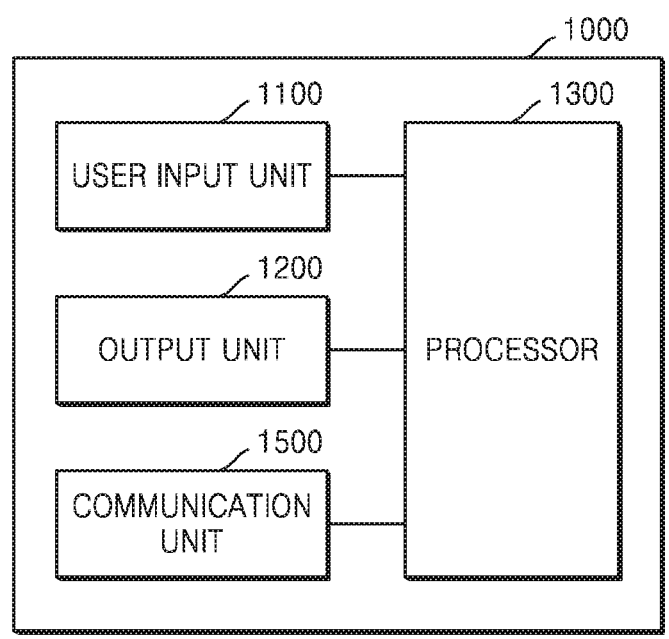
FIGS. 16 and 17 are block diagrams of an electronic device, according to an embodiment.
Figure 17:
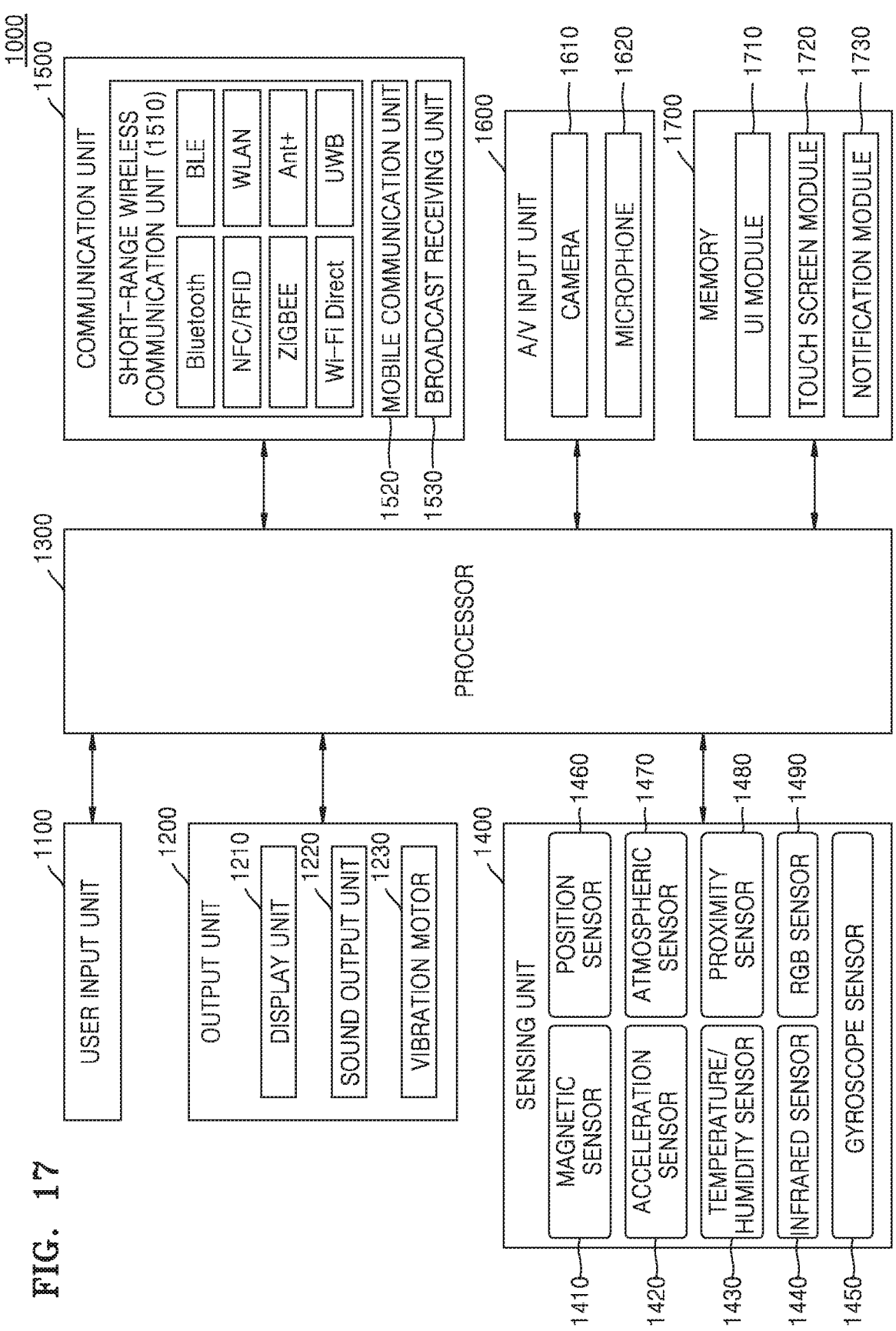

FIGS. 16 and 17 are block diagrams of the electronic device 1000 according to some embodiments.

As shown in FIG. 16, the electronic device 1000 according to some embodiments may include a user input unit 1100, an output unit 1200, a processor 1300, and a communication unit 1500. However, not all components shown in FIG. 16 are essential components of the electronic device 1000. The electronic device 1000 may include more than those shown in FIG. 16, or may include less than those shown in FIG. 16.

For example, as shown in FIG. 17, the electronic device 1000 according to some embodiments may further include a sensing unit 1400, an audio/video (A/V) input unit 1600, and a memory 1700 in addition to the user input unit 1100, the input unit 1200, the processor 1300, and the communication unit 1500.

The user input unit 1100 denotes a unit into which a user inputs data for controlling the electronic device 1000. Examples of the user input unit 1100 may include a keypad, a dome switch, a touch pad (a touch capacitance type, a pressure resistance film type, an infrared light detecting type, a surface ultrasound conducting type, an integral tension measuring type, or a piezo-effect type), a jog wheel, and a jog switch, but are not limited thereto.

The user input unit 1100 may receive a user input for enabling the electronic device 1000 to obtain an image of an object, determine a skin type of the object, and provide recommendation information related to skin.

The output unit 1200 may output an audio signal, a video signal, or a vibration signal, and may include a display unit 1210, a sound output unit 1220, and a vibration motor 1230.

The display unit 1210 displays information processed by the electronic device 1000. For example, the display unit 1210 may display a user interface for obtaining the image of the object, determining the skin type of the object, and providing the recommendation information related to the skin.

Meanwhile, when the display unit 1210 is configured as a touch screen by forming a layer structure with a touch pad, the display unit 1210 may also be used as an input device as well as an output device. The display unit 1210 may include at least one of a liquid crystal display (LCD), a thin-film-transistor liquid-crystal display (TFT-LCD), an organic light-emitting diode (OLED), a flexible display, a 3D display, and an electrophoretic display. Also, according to an embodiment of the electronic device 1000, the electronic device 1000 may include at least two display units 1210.

The sound output unit 1220 outputs audio data received from the communication unit 1500 or stored in the memory 1700. Also, the sound output unit 1220 outputs a sound signal related to a function performed by the electronic device 1000, such as a call signal reception sound, a message reception sound, or an alarm sound.

The vibration motor 1230 may output a vibration signal. For example, the vibration motor 1230 may output a vibration signal corresponding to an output of audio data or video data (for example, a call signal reception sound or a message reception sound).

The processor 1300 controls overall operations of the electronic device 1000. For example, the processor 1300 may generally control the user input unit 1100, the output unit 1200, the sensing unit 1400, the communication unit 1500, and the AN input unit 1600 by executing programs stored in the memory 1700. Also, the processor 1300 may control operations of the electronic device 1000 described in FIGS. 1 through 16.

In detail, the processor 1300 may obtain the image of the object. The processor 1300 may image the object by controlling a camera 1610 described below and obtain the image of the object. Alternatively, the camera 1300 may receive the image of the object from an external device (not shown) or a server (not shown) by controlling the communication unit 1500.

The processor 1300 may distinguish a skin portion and a non-skin portion of the object from the image of the object, and determine a skin type of the object based on colors of the skin portion and non-skin portion of the object. In this case, also, the skin portion of the object and the non-skin portion of the object may be pre-set according to predetermined standards, and information for distinguishing the skin portion of the object and the non-skin portion of the object from the image of the object may be pre-stored in the memory 1700.

Also, the processor 1300 may determine at least one skin attribute related to the object, and determine a skin type of the object based on the determined skin attribute. In this case, the processor 1300 may determine a color ratio of the skin portion to the non-skin portion from the image of the object, and determine the skin type of the object based on the determined skin attribute and the determined color ratio.

Also, the processor 1300 may provide recommendation information related to skin of the user based on the determined skin type. The processor 1300 may provide the recommendation information related to the skin of the user considering environment information around the object and/or the skin attribute of the object.

The processor 1300 may obtain the environment information around the object. According to an embodiment, the environment information may include a current time, a current weather, a current location, existence of a lighting system in an object surrounding environment, and direct exposure to the sun.

The processor 1300 may obtain the recommendation information for managing the skin of the object by using at least one of the skin type, skin attribute, and environment information of the object, and output the recommendation information through the output unit 1200.

The sensing unit 1400 may detect a state of the electronic device 1000 or a state around the electronic device 1000, and transmit detected information to the processor 1300.

The sensing unit 1400 may include at least one of a magnetic sensor 1410, an acceleration sensor 1420, a temperature/humidity sensor 1430, an infrared sensor 1440, a gyroscope sensor 1450, a position sensor 1460 (for example, a global positioning system (GPS)), an atmospheric sensor 1470, a proximity sensor 1480, and a red, green, blue (RGB) sensor 1490, but components included in the sensing unit 1400 are not limited thereto. Because functions of each sensor may be intuitively inferred by one of ordinary skill in the art based on its name, details thereof are not described herein.

In order to enable the electronic device 1000 to obtain the image of the object, determine the skin type of the object, and provide the recommendation information related to the skin, the communication unit 1500 may include one or more components communicating with an external device (not shown) and/or a server (not shown). For example, the communication unit 1500 may include a short-range wireless communication unit 1510, a mobile communication unit 1520, and a broadcast receiving unit 1530.

The short-range communication unit 1510 may include a Bluetooth communication unit, a Bluetooth low energy (BLE) communication unit, a near-field communication (NFC) unit, a wireless local area network (WLAN) (Wi-Fi) communication unit, a Zigbee communication unit, an infrared data association (IrDA) communication unit, a Wi-Fi direct (WFD) communication unit, an ultra-wideband (UWB) communication unit, and an Ant+ communication unit, but components included in the short-range communication unit 1510 are not limited thereto.

The mobile communication unit 1520 transmits and receives a wireless signal to and from at least one of a base station, an external terminal, and a server, on a mobile communication network. Here, a wireless signal may include data having various formats according to transmission and reception of a voice call signal, a video telephone call signal, or a text/multimedia message.

The broadcast receiving unit 1530 receives a broadcast signal and/or broadcast related information from an external source, through a broadcast channel. The broadcast channel may include a satellite channel or a terrestrial broadcasting channel. According to an embodiment, the electronic device 1000 may not include the broadcast receiving unit 1530.

Also, the communication unit 1500 may transmit and receive information required to obtain the image of the object, determine the skin type of the object, and provide the recommendation information related to the skin to and from an external device (not shown) and/or a server (not shown).

The A/V input unit 1600 receives an audio signal or a video signal, and may include the camera 1610 and a microphone 1620. The camera 1610 may obtain an image frame of a still image or a moving image via the image sensor in a video telephone mode or an imaging mode. An image captured via the image sensor may be processed by the processor 1300 or a separate image processor (not shown).

According to an embodiment of a terminal, there may be at least two cameras 1610. The camera 1610 may be controlled by the processor 1300 to image the object and generate the image of the object.

The microphone 1620 receives an external sound signal and processes the external sound signal to electric voice data.

The memory 1700 may store programs for processes and controls of the processor 1300, and may store data input to or output from the electronic device 1000.

The memory 1700 may include at least one type of storage medium from among a flash memory, a hard disk, a multimedia card micro-type memory, a card-type memory (for example, a secure digital (SD) card or an extreme digital (XD) card), a random-access memory (RAM), a static random-access memory (SRAM), a read-only memory (ROM), an electrically erasable programmable read-only memory (EEPROM), a programmable read-only memory (PROM), a magnetic memory, a magnetic disk, and an optical disk.

Programs stored in the memory 1700 may be classified into a plurality of modules based on functions, and for example, may be classified into a user interface (UI) module 1710, a touch screen module 1720, and a notification module 1730.

The UI module 1710 may provide a specialized UI or GUI linked to the electronic device 1000 according to applications. The touch screen module 1720 may detect a touch gesture of a user on a touch screen, and transmit information about the touch gesture to the processor 1300. The touch screen module 1720 according to an embodiment may recognize and analyze a touch code. The touch screen module 1720 may be configured as separate hardware including a processor.

The notification module 1730 may generate a signal for notifying event generation in the electronic device 1000. Examples of an event that is generated in the electronic device 1000 include call signal reception, message reception, key signal input, and schedule notification. The notification module 1730 may output a notification signal in a video signal format through the display unit 1210, in an audio signal format through the sound output unit 1220, or in a vibration signal format through the vibration motor 1230.

Some embodiments may also be realized in a form of a computer-readable recording medium, such as a program module executed by a computer. A computer-readable recording medium may be an arbitrary available medium accessible by a computer, and examples thereof include all volatile and non-volatile media and separable and non-separable media. Further, examples of the computer-readable recording medium may include a computer storage medium and a communication medium. Examples of the computer storage medium include all volatile and nonvolatile media and separable and non-separable media, which have been implemented by an arbitrary method or technology, for storing information such as computer-readable commands, data structures, program modules, and other data. The communication medium typically include a computer-readable command, a data structure, a program module, other data of a modulated data signal, or another transmission mechanism, and an example thereof includes an arbitrary information transmission medium.

Also, in the present specification, a "unit" may be a hardware component, such as a processor or a circuit, and/or a software component executed by a hardware component, such as a processor.

While the present disclosure has been particularly shown and described with reference to exemplary embodiments thereof, it will be understood by one of ordinary skill in the art that various changes in form and details may be made therein without departing from the technical ideas and essential features of the present disclosure. Hence, it will be understood that the embodiments described above are not limiting the scope of the disclosure. For example, each component described in a single type may be executed in a distributed manner, and components described distributed may also be executed in an integrated form.

The scope of the present disclosure is indicated by the claims which will be described in the following rather than the detailed description of the disclosure, and it should be understood that the claims and all modifications or modified forms drawn from the concept of the claims are included in the scope of the present disclosure.

The invention claimed is:

1. An electronic device for determining a skin type of an object, the electronic device comprising:
   a camera;
   a memory storing one or more instructions; and
   a processor configured to execute the one or more instructions to:
      control the camera to capture at least one image comprising a skin portion and a non-skin portion of an object;
      determine a characteristic vector comprising at least one color ratio between the skin portion and the non-skin portion according to a plurality of pre-set color elements and a non-color characteristic;
      determine at least one skin attribute related to the object from the captured at least one image; and
      determine, by using the characteristic vector, a skin type representing a color ratio similar to the at least one color ratio in a skin type table corresponding to the determined at least one skin attribute as a skin type of the object.

2. The electronic device of claim 1, wherein the processor is further configured to:
   extract at least one skin type table corresponding to the determined at least one skin attribute; and
   determine the skin type of the object using the extracted at least one skin type table and the at least one color ratio of the object.

3. The electronic device of claim 1, wherein the at least one skin attribute comprises at least one of a disease related to the skin portion, a disease related to the non-skin portion, a skin tanning state of the object, and an amount of oily residue on skin of the object and wherein the non-skin portion comprises at least one of a fingernail portion and a conjunctiva portion.

4. The electronic device of claim 1, wherein the plurality of pre-set color elements comprise at least two of red, green, blue, hue, saturation, and brightness (value) ($RGB_{13}$ HSV).

5. The electronic device of claim 1, wherein the processor is further configured to provide recommendation information for managing skin of the object based on the determined skin type.

6. The electronic device of claim 5, wherein the processor is further configured to:
   obtain environment information about an environment around the object, and
   determine the recommendation information based on at least one of the environment information, the determined skin attribute and the determined skin type.

7. The electronic device of claim 6, wherein the recommendation information comprises at least one of information for avoiding sunburn, information about a sunscreen suitable to the object, and information about a recommended length of time for the object to be exposed to sun.

8. The electronic device of claim 1, wherein the processor is further configured to:
   determine a parameter corresponding the determined at least one skin attribute;
   compensate the at least one color ratio using the determined parameter; and
   determine the skin type of the object using a predetermined skin type table and the compensated at least one color ratio of the object.

9. The electronic device of claim 1, wherein the processor is further configured to:
   obtain information about the skin portion of the object based on a user input responding to a survey for the skin portion of the object; and
   obtain score information by assigning a score per item of the survey using the obtained information about the skin portion of the object, wherein the skin type table is generated by using at least some of the obtained score information, wherein the at least one skin attribute is determined by using at least some of the obtained score information.

10. A method of determining, by an electronic device, a skin type of an object, the method comprising:
   obtaining at least one captured image comprising a skin portion and a non-skin portion of an object;
   determining at least one skin attribute related to the object;
   determining a characteristic vector comprising at least one color ratio between the skin portion and the non-skin portion from the captured at least one image according to a plurality of pre-set color elements and a non-color characteristic; and
   determining, by using the characteristic vector, a skin type representing a color ratio similar to the at least one color ratio in a skin type table corresponding to the determined at least one skin attribute as a skin type of the object.

11. The method of claim 10, further comprising extracting at least one skin type table corresponding to the determined at least one skin attribute; and
   determining the skin type of the object using the extracted at least one skin type table and the at least one color ratio of the object.

12. The method of claim 11, further comprising:
   determining a parameter corresponding the determined at least one skin attribute;
   compensating the at least one color ratio using the determined parameter; and
   determining the skin type of the object using a predetermined skin type table and the compensated at least one color ratio of the object.

13. The method of claim 10, wherein, in the determining of the at least one color ratio, the at least one color ratio between the skin portion and the non-skin portion is determined according to a plurality of pre-set color elements.

14. The method of claim 10, wherein the plurality of pre-set color elements comprise at least two of red, green, blue, hue, saturation, and brightness (value) (RGB_HSV).

15. The method of claim 14, further comprising:
   calculating a characteristic vector comprising the at least one color ratio according to the plurality of pre-set color elements and a non-color characteristic; and
   determining the skin type of the object using the calculated characteristic vector and the extracted at least one skin type table.

16. The method of claim 10, wherein the at least one skin attribute comprises at least one of a disease related to the skin portion, a disease related to the non-skin portion, a skin tanning state of the object, and an amount of oily residue on skin of the object and wherein the non-skin portion comprises at least one of a fingernail portion and a conjunctiva portion.

17. The method of claim 10, further comprising:
obtaining environment information about an environment around the object;
providing recommendation information for managing skin of the object based on at least one of the environment information, the determined skin attribute or the determined skin type.

18. A non-transitory computer-readable recording medium having recorded thereon a program which, when executed by a computer, performs a method comprising:
obtaining at least one captured image comprising a skin portion and a non-skin portion of an object;
determining at least one skin attribute related to the object;
determining a characteristic vector comprising at least one color ratio between the skin portion and the non-skin portion from the captured at least one image according to a plurality of pre-set color elements and a non-color characteristic; and determining, by using the characteristic vector, a skin type representing a color ratio similar to the at least one color ratio in a skin type table corresponding to the determined at least one skin attribute as a skin type of the object.

* * * * *